United States Patent [19]

Polouchine

[11] Patent Number: 5,902,879

[45] Date of Patent: May 11, 1999

[54] METHOXYOXALAMIDO AND SUCCINIMIDO PRECURSORS FOR NUCLEOPHILIC ADDITION TO NUCLEOSIDES, NUCLEOTIDES AND OLIGONUCLEOTIDES

[75] Inventor: Nikolai N. Polouchine, Rockville, Md.

[73] Assignee: Fidelity Systems, Inc., Gaithersburg, Md.

[21] Appl. No.: 08/692,284

[22] Filed: Aug. 5, 1996

[51] Int. Cl.$^6$ .............................. C07H 1/00; C07H 19/00; C07H 21/00

[52] U.S. Cl. .................... 536/23.1; 536/25.3; 536/25.31; 536/25.34; 536/26.26; 536/26.6; 536/26.7; 536/26.8; 536/27.6; 536/27.8; 536/27.81; 536/28.1; 536/28.5; 536/28.53; 536/28.54; 536/124

[58] Field of Search ............................... 536/25.3, 25.31, 536/25.34, 23.1, 26.26, 26.6, 26.7, 26.8, 27.6, 27.8, 27.81, 28.1, 28.5, 28.53, 28.54, 124

[56] References Cited

U.S. PATENT DOCUMENTS

| | | |
|---|---|---|
| 5,112,962 | 5/1992 | Letsinger et al. . |
| 5,466,786 | 11/1995 | Buhr et al. . |
| 5,547,835 | 8/1996 | Köster .................................... 536/25.3 |

OTHER PUBLICATIONS

V.A. Efimov, "Recent Developments in the Synthesis of Oligonucleotides, Their Analogues and Conjugates", *Nucleic Acids Symposium* (Aug. 6–11, 1995).

N.N. Polushin, "Synthesis of Functionally Modified Oligonucleotides Through 2'-Methoxyoxalamide-2'-Deoxyuridine Containing Precursors", *Nucleic Acids Symposium* (Aug. 6–11, 1995).

N. N. Polushin, "Synthesis of Functionally Modified Oligonucleotides from Methoxyoxalamido Precursors", *Tetrahedron Letters*, vol. 37, No. 19, pp. 3231–3234, (1996).

N. N. Polushin, "Synthesis of Oligonucleotides Containing 2'-Azido– and 2'-Amino–2'-deoxyuridine Using Phosphotriester Chemistry", *Tetrahedron Letters*, vol. 37, No. 19, pp. 3227–3230, (1996).

N. Herbert, "Synthesis of N–Substituted Hydroxyprolinol Phosphoramidites for the Preparation of Combinatorial Libraries", *Tetrahedron Letters*, vol. 35, No. 51, pp. 9509–9512, (1994).

P. W. Davis, "Drug Leads from Combinatorial Phosphodiester Libraries", *J. Med. Chem.*, vol. 38, pp. 4363–4366, (1995).

A. M. MacMillan, "Synthesis of Functionally Tethered Oligodeoxynucleotides by the Convertible Nucleoside Approach", *J. Org. Chem*, vol. 55, pp. 5931–5933, (1990).

L. Biegelman et al., "Synthesis of 2'-modified Nucleotides and their Incorporation into Hammerhead Ribozymes", *Nucleic Acids Research*, vol. 23, No. 21, pp. 4434–4442, (1995).

N. N. Polushin et al., "Synthesis and Characterization of Imidazoyl–Linked Synthons and 3'–Conjugated Thymidine Derivatives", *Journal of Organic Chemistry*, vol. 58, pp. 4606–4613, (1993).

R. H. Alul, "Oxalyl–CPG: a labile support for synthesis of sensitive oligonucleotide derivatives", *Nucleic Acids Research*, vol. 19, No. 9, pp. 1527–1532, (1991).

A. M. MacMillan et al., "Engineering Tethered DNA Molecules by the Convertible Nucleoside Approach", *Tetrahedron Letters*, vol. 47, No. 14/15, pp. 2603–2616, (1991).

A. E. Ferentz et al., "Aminolysis of 2'–Deoxyinosine Aryl Ethers: Nucleoside Model Studies for the Synthesis of Functionally Tethered Oligonucleotides", *Nucleosides & Nucleotides*, vol. 11, No. 10, pp. 1749–1763, (1992).

F. Benseler et al., "Synthesis of Suitably–protected Phosphoramidites of 2'–Fluoro–2'–Deoxyguanosine and 2'–Amino–2'–Deoxyguanosine for Incorporation into Oligoribonucleotides", *Nucleosides & Nucleotides*, vol. 11, No. 7, pp. 1333–1351, (1992).

I. P. Smirnov et al., "Sequencing Oligonucleotides by Exonuclease Digestion and Delayed Extraction Matrix–Assisted Laser Desorption Ionization Time–of–Flight Mass Spectrometry", *Analytical Biochemistry*, vol. 288, pp. 19–25, (1996).

J. Goodchild, "Conjugates of Oligonucleotides and Modified Oligonucleotides: A Review of Their Synthesis and Properties", *Perspectives in Bioconjugate Chemistry*, pp. 77–99, (1993).

V.A. Efimov et al., "New Activators for the Phosphoramidite Oligonucleotide Synthesis", vol. 22, No. 2, (1996).

*Primary Examiner*—James O. Wilson
*Attorney, Agent, or Firm*—Oliff & Berridge, PLC

[57] ABSTRACT

Moieties, including a 2'-methoxyoxalamido and N-succinimido moieties, were incorporated into a compound, particularly an oligonucleotide molecule. The moieties were shown to be useful precursors for the post synthetic introduction of various functional additives.

19 Claims, 2 Drawing Sheets

METHOXYOXALAMIDO AND SUCCINIMIDO PRECURSORS FOR NUCLEOPHILIC ADDITION TO NUCLEOSIDES, NUCLEOTIDES AND OLIGONUCLEOTIDES

BACKGROUND OF THE INVENTION

A precursor strategy is a system by which a single precursor is used to manufacture a variety of different products. The use of a precursor strategy is quite common in synthetic organic chemistry.

As used herein, a precursor is a molecule capable of reacting with different compounds, such as modifiers, to produce a number of different products. A precursor molecule comprises a core and one or more reactive moieties. The "core" is the part of the compound that does not generally change and the part that often, but not necessarily, possesses some specific properties critical for the desired application. Thus, the core is generally untouched upon reaction with a modifier.

A "reactive moiety" is a group that reacts in a highly effective, preferably quantitative, and specific manner with a particular modifier to form a particular product or with a mixture of modifiers to form a pool of products. If a core part of a precursor contains some functionalities that are also capable of reacting with the modifier, these functionalities must be protected.

A precursor strategy will work successfully only if some demands are fulfilled. These demands include the following:

1. If a precursor is a complex molecule and is prepared by multi-step synthesis, the precursor reactive moiety or moieties must be stable in all conditions used during the synthesis after its introduction. However, this rule is not applicable if a reactive moiety is introduced at the very last step of the precursor synthesis.
2. It is highly desirable for the yield of the reaction between a precursor reactive moiety and a modifier to be close to quantitative. This is especially important when the precursor contains more than one reactive moiety.
3. The core part of a precursor must be stable in the conditions of transformation, that is, the conditions under which the precursor reacts with a modifier.
4. One or more a modified site, that is, parts of a product molecule that are formed after reaction between a precursor reactive moiety and a modifier, must tolerate the deprotection conditions if a deprotection step is necessary to prepare a desired product.
5. It is desirable for the transformation time to be relatively short.

Oligonucleotides bearing various functionalities have become common place tools in molecular biology and diagnostics. Goodchild, J., "Conjugates of Oligonucleotides and Modified Oligonucleotides: A Review of Their Synthesis and Properties," *Perspectives in Bioconjugate Chemistry*, pp. 77–99 (1993). One of the most efficient routes to the synthesis of functionally modified oligonucleotides (FMOs) is the introduction of a precursor, that is, a nucleotide monomer bearing a reactive moiety, into the oligonucleotide. At the end of solid phase synthesis, the precursor reacts with a desired linker or modifier. This strategy enables one to synthesize a wide variety of FMOs from a single parent oligonucleotide.

MacMillan, A. and Verdine, G., "Engineering Tethered DNA Molecules by the Convertible Nucleoside Approach," *Tetrahedron*, 47: 2603–2619 (1991), and Ferenz, A. and Verdine, G., "Aminolysis of 2'-Deoxyinosine Aryl Ethers: Nucleoside Model Studies for the Synthesis of Functionally Tethered Oligonucleotides," *Nucleosides & Nucleotides*, 11: 1749–1763 (1992), have elaborated a convertible nucleoside strategy to prepare functionally tethered oligonucleotides (FTOs). This convergent strategy is based on the use of O-substituted deoxyuridine and deoxyinosine as convertible nucleosides. Upon treatment with aqueous amines, precursor oligonucleotides containing convertible nucleosides undergoes a transformation giving rise to a FTO.

Buhr et al., U.S. Pat. No. 5,466,786, described the incorporation of a 2'-deoxy-2'-O-(ethoxycarbonylmethyl)-cytidine into an oligonucleotide. After solid phase synthesis and deprotection, the ester group, which is a reactive moiety, can be hydrolyzed to a carboxy group by treatment with NaOH or derivatized to an amide or substituted amide by a reaction with $NH_3$ or a primary aliphatic amine.

Hebert et al., *Tetrahedron Letters*, 35: 9509–9512 (1994), reported the N-acylation of a DMT-hydroxymethylpyrrolidinol precursor with a number of carboxylic acids. N-substituted DMT-hydroxymethylpyrrolidinols were further phosphitilated and used for the preparation of phosphodiester oligomer combinatorial libraries.

SUMMARY OF THE INVENTION

The present invention is directed to a method for attaching a nucleophile to a compound, comprising:

reacting a first compound containing a first moiety selected from the group consisting of —COCOOCR$_3$, —COCR$_2$CR$_2$CO—, —COCR=CRCO— and —COSSCO— with a second compound containing a primary or secondary amine, which may or may not be an amino substituted nucleoside or nucleotide, to form a third compound containing a second moiety selected from the group consisting of —NRCOCOOCR$_3$, said first moiety attaching to a nitrogen of the amine to form said second moiety, wherein each R independently represents H or a substituted or unsubstituted alkyl group;

reacting a protonated nucleophile (HNu) with the second moiety of said third compound to form a fourth compound containing a third moiety selected from the group consisting of: —NRCOCONu, —NHCOCR$_2$CR$_2$CONu, —NHCOCR=CRCONu and —NHCOSSCONu.

The present invention is also directed to a method for forming an oligomer or polymer, comprising:

reacting a compound containing a first moiety selected from the group consisting of —COCOOCR$_3$, —COCR$_2$CR$_2$CO—, —COCR=CRCO— and —COSSCO— with a first monomer containing a primary or secondary amine, which may or may not be an amino substituted nucleoside or nucleotide, to form a second monomer containing a second moiety selected from the group consisting of —NRCOCOOCR$_3$, said first moiety attaching to a nitrogen of the amine to form said second moiety, wherein each R independently represents H or a substituted or unsubstituted alkyl group;

reacting said second monomer with at least one other monomer to form an oligomer or polymer;

reacting a protonated nucleophile (HNu) with the second moiety to form a third moiety in said oligomer or polymer, said third moiety being selected from the group consisting of: —NRCOCONu, —NHCOCR$_2$CR$_2$CONu, —NHCOCR═CRCONu and —NHCOSSCONu.

The present invention is further directed to a compound having the formula (I):

(I)

wherein A represents an organic moiety, each X independently represents H, a group that protects a hydroxy group, a (PO$_3$)$_m$$^{-2}$ group wherein m is a integer of 1–3, a group reactive to link hydroxy groups, or a phosphodiester linkage to a another compound, R' is selected from the group consisting of: —NRCOCONu, —NHCOCR$_2$CR$_2$CONu, —NHCOCR═CRCONu, —NHCOSSCONu, —NRCOCOOCR$_3$, wherein each R independently represents H or a substituted or unsubstituted alkyl group and Nu represents a nucleophile.

Additionally, the present invention is directed to a nucleoside or nucleotide having the formula (II):

(II)

wherein B is a purine or pyrimidine moiety, each X independently represents H, a group that protects a hydroxy group, a (PO$_3$)$_m$$^{-2}$ group wherein m is a integer of 1–3, a group reactive to link hydroxy groups, or a phosphodiester linkage to a another compound, R' is selected from the group consisting of: —NRCOCONu, —NHCOCR$_2$CR$_2$CONu, —NHCOCR═CRCONu, —NHCOSSCONu, —NRCOCOOCR$_3$, wherein each R independently represents H or a substituted or unsubstituted alkyl group and. Nu represents a nucleophile.

Finally, the present invention is directed an oligomer or polymer, which may or may not be an oligonucleotide or polynucleotide that contains at least one compound having the formula (I).

DETAILED DESCRIPTION OF THE INVENTION

The present invention is directed to a method for attaching a nucleophile to a compound. In the method, a first compound containing a first moiety selected from the group consisting of —COCOOCR$_3$, —COCR$_2$CR$_2$CO—, —COCR═CRCO— and —COSSCO— is reacted with a second compound containing a primary or secondary amine. By this reaction, a third compound containing a second moiety selected from the group consisting of —NRCOCOOCR$_3$, is formed.

In the first moiety, each R independently represents H or a substituted or unsubstituted alkyl group. In a preferred embodiment of the invention, the moiety is a methoxyoxalamido moiety, that is, each R in the moiety is an H. In embodiments of the invention where the R is a substituted or unsubstituted alkyl group, the alkyl group may contain from 1 to 15, preferably from 1 to 12, and more preferably from 1 to 6 carbon atoms.

In the first compound, the group or groups attached to each of the first moieties can be any group as long as the carbon atom of the first compound attached to that group can be made to react with the amino group of the second compound. In particular, a strong nucleophile may be attached to the moiety. A strong nucleophile includes a methoxy group or a group that is a stronger nucleophile than a methoxy group. For example, chlorine and/or tetrazole may be attached to the moiety.

Where the first moiety is —COCOOCR$_3$, the group attached to the moiety may be identical to or a stronger nucleophile than the —OCR$_3$ group of the moiety. Thus, where each R in the moiety is a H, the group attached to the moiety may be a methoxy group or a group that is a stronger nucleophile than a methoxy group. Therefore, where the —OCR$_3$ group of the moiety is a weaker nucleophile than a methoxy group, the group attached to the moiety may be a weaker nucleophile than methoxy as long as it identical to or a stronger nucleophile than the —OCR$_3$ group in the moiety. Thus, in an embodiment of the invention the first compound is R$_3$COCOCOOCR$_3$, preferably H$_3$COCOCOOCH$_3$.

The second compound contains a primary or secondary amine. In an embodiment of the invention, the amine is a primary amine. A primary amine is particularly preferred where the first moiety of the first compound is —COCR$_2$CR$_2$CO—, —COCR=CRCO— or —COSSCO—. In a preferred embodiment of the invention, the carbon attached to the amino group is an aliphatic carbon.

The second compound may be any compound containing an amine as long as the amine is susceptible to reaction with the first compound. In an embodiment to the invention, the second compound is a nucleoside or nucleotide containing an amino group. In a preferred embodiment of the invention, the amino group is attached to a carbon atom of the ribose or deoxyribose sugar of the nucleoside or nucleotide. In a further preferred embodiment, the amino group is attached to the 2' position of the sugar.

In the method of the present invention, the third compound containing a second moiety selected from the group consisting of —NRCOCOOCR$_3$, is reacted with a protonated nucleophile (HNu) to form a fourth compound containing a third moiety selected from the group consisting of: —NRCOCONu, —NHCOCR$_2$CR$_2$CONu, —NHCOCR=CRCONu and —NHCOSSCONu. In particular, the second moiety of the third compound reacts with the protonated nucleophile.

In a preferred embodiment of the invention, the protonated nucleophile is selected from the group consisting of ammonia, primary amines, secondary amines and a hydroxy group.

By using the above method, an oligomer or polymer containing at least one moiety selected from the group consisting of: —NRCOCONu, —NHCOCR$_2$CR$_2$CONu, —NHCOCR=CRCONu and —NHCOSSCONu can be formed. To form the oligomer or polymer, a compound containing a first moiety selected from the group consisting of —COCOOCR$_3$, —COCR$_2$CR$_2$CO—, —COCR=CRCO— and —COSSCO— is reacted with a first monomer containing a primary or secondary amine to form a second monomer containing a second moiety selected from the group consisting of —NRCOCOOCR$_3$, The second monomer is then reacted with at least one other monomer to form an oligomer or polymer. The other monomers may or may not contain a moiety selected from the group consisting of: —NRCOCOOCR$_3$, After the oligomer or polymer is formed, it is reacted with a protonated nucleophile (HNu) to form an oligomer or polymer containing a third moiety selected from the group consisting of: —NRCOCONu, —NHCOCR$_2$CR$_2$CONu, —NHCOCR=CRCONu and —NHCOSSCONu.

In an embodiment of the invention, the monomers contains at least two hydroxy or protected hydroxy groups. In a "protected hydroxy group," the H in the hydroxy group is replaced with a "protecting group." A "protecting group" in this context is a substituent that prevents the reactivity of the —OH during a reaction, but that can be removed when the reaction is completed. In particular, a protecting group prevents a reaction to link sequential nucleotides. Typical protecting groups in the compounds of the invention include 4,4'-dimethoxy trityl (DMT), 4-monomethoxytrityl and trityl.

Monomers that contain at least two hydroxy or protected hydroxy groups can undergo polymerization reactions that link the hydroxy groups. In an embodiment of the invention, phosphodiester linkages between the monomers may be formed by phosphitilation techniques known in the art.

In an embodiment of the invention, the first monomer is a nucleoside or nucleotide that has an amino group substituted on, for example, at least one position of the sugar. Known phosphitilation techniques may be used to form phosphodiester linkages between the monomer and other nucleosides or nucleotides, which may or may not be a monomer of the present invention, such that oligonucleotides or polynucleotides can be formed.

In a preferred embodiment of the invention, oligonucleotides or polynucleotides are formed using a phosphoramidite method. 1-phenyl-1H-tetrazole-5-thiol (PTT) is a preferred catalyst in the phosphoramidite method. Efimov, V., "Recent Developments in the Synthesis of Oligonucleotides, their Analogues and Conjugates," *Nucleic Acids Symposium*, The Netherlands (1995). In a further preferred embodiment of the invention, a double mode coupling protocol is used. A double mode coupling protocol means that there are two consecutive coupling steps, with only washing in between the coupling steps. In contrast, in the standard phosphoramidite method, capping occurs between each coupling reaction.

The present invention is also directed to compounds formed by the claimed processes. In particular, the present invention is directed to a compound having the formula (I):

(I)

wherein A represents an organic moiety, each X independently represents H, a group that protects a hydroxy group (that is, a "protecting group" as defined above), a (PO$_3$)$_m^{-2}$ group wherein m is a integer of 1–3, a group reactive to link hydroxy groups, or a phosphodiester linkage to a another compound, R' is selected from the group consisting of: —NRCOCONu, —NHCOCR₂CR₂CONu, —NHCOCR=CRCONu, —NHCOSSCONu, —NRCOCOOCR₃, wherein each R independently represents H or a substituted or unsubstituted alkyl group and Nu represents a nucleophile.

A "group reactive to link hydroxy groups" is an intermediate residue in the formation of a link, particularly an internucleotide link, between hydroxy groups, particularly the 5' and 3' hydroxyls. The group is typically a phosphorus containing group, such as a phosphoramidite group. The reaction of the group with a —OH of a adjacent monomer results in a linking residue, particularly a nucleotide linking residue. The linking residue may be any linking moiety conventionally used to conjugate hydroxy groups of adjacent monomers, particularly, to conjugate nucleotide residues.

In an additional embodiment of the invention, the compound is a nucleoside or nucleotide having the formula (II):

(II)

wherein X and R' are as described above and B is a purine or pyrimidine moiety.

In an embodiment of the invention, B represents a conventional purine or pyrimidine base such as adenine (A), thymine (T), cytosine (C), guanine (G), or uracil (U) or protected forms thereof. Suitable protecting groups include acyl, isobutyryl, benzoyl, and the like. B can, however, also represent a modified or related derivative of these conventionally occurring bases.

In a further embodiment of the invention, at least one X represents a dimethoxytrityl group.

In an additional embodiment of the invention, the compound is a nucleoside joined through a phosphodiester linkage to at least one other nucleoside to form a oligonucleotide or a polynucleotide.

The present invention is also directed to a compound having the formula (III):

A—R'  (III)

wherein A represents an organic moiety, R' is selected from the group consisting of: —NRCOCONu, —NHCOCR₂CR₂CONu, —NHCOCR=CRCONu, —NHCOSSCONu, —NRCOCOOCR₃, each R independently represents H or a substituted or unsubstituted alkyl group, and Nu represents a nucleophile. In a preferred embodiment of the invention, the organic moiety is part of an oligomer or polymer.

In an embodiment of the invention, the nucleophile is selected form the group consisting of —O⁻, an amino group (—NH₂), a primary amino group (—NRH) and a secondary amino group (—NR₂). R may be a substituted or unsubstituted alkyl group. The alkyl group may preferably have from 1 to 15, more preferably from 1 to 12, and even more preferably from 1 to 6 carbon atoms.

The present invention is also directed to conjugate acids and salts of the compounds of the present invention. In particular, the nucleophillic groups may be bonded to a proton or a cation to form an acid or salt. For example, the present invention is directed to compounds having the following moieties: —OH, —NH₃⁺, —NRH₂⁺, —NR₂H⁺ and —OX, where X is a cation.

The use of nucleosides, particularly methoxyoxalamido and N-succinimido moieties, in the precursor strategy defined herein is described below. However, the invention is not limited to these embodiments.

Methoxyoxalamidoalkyl and N-succinimidoalkyl moieties can act as reactive moieties in a precursor strategy if designed as a part of a precursor molecule. In particular, they have potential as a precursor for the post synthetic introduction of various effectors onto an oligonucleotide molecule.

In a methoxyoxalamido moiety, the ester carbonyl carbon of the methoxyoxalyl residue is highly electrophilic due to electron withdrawing effects of the adjacent methoxy and carbonyl groups. Thus, the attack of nucleophiles onto this electrophilic center occurs very quickly and efficiently. In fact, it is close to quantitative in minutes or less. This was demonstrated by reaction of 5'-dimethoxytrityl-2'-methoxyoxalamido-2'-deoxyuridine with ethanolamine, aqueous ammonia and the acetonitrile solution of 1,8-diazabicyclo[5,4,0]undec-7-ene in the presence of water (DBUH⁺OH⁻).

-continued

The methoxyoxalamidoalkyl moiety, if designed as part of an oligonucleotide molecule, is a convenient site for the introduction of various functional additives. Thus, a desirable modifier, particularly if it contains an aliphatic amino group, may easily derivatize a methoxyoxalamido precursor at a methoxyoxalyl site to afford the corresponding conjugate via a stable alkylamidooxalamidoalkyl bridge (alkyl-NHCOCONH-alkyl).

In the methoxyoxalamido moiety, any of the hydrogen atoms may be substituted with an alkyl radical (NRCOCOOCR$_3$, R=alkyl). The alkyl group may be substituted or unsubstituted. Preferably, the alkyl group contains 1–12, more preferably 1–6, carbon atoms.

1. 2'-Modified Nucleosides and Their Combinatorial Libraries

A. From methoxyoxalamido precursors. A mechanism by which the present invention may be practiced is demonstrated below. Although specific groups, such as uracil, are demonstrated in this mechanism, the invention is not limited thereto.

stituted or unsubstituted. Preferably, the alkyl group contains 1–12, more preferably 1–6, carbon atoms.

In a N-succinimido moiety, both carbonyl carbons of the N-succinimide moiety are equally highly electrophilic due to electron withdrawing effects of the carbonyl groups. The nucleophilic cycle opening, that is, the attack of a nucleophile onto one of the carbonyl carbons, proceeds very rapidly, usually within seconds, and in a quantitative yield. On the other hand, the amidoethyleneamido bridge (—NHCOCH$_2$CH$_2$CONH—), which is formed between the modifier and the precursor core, is stable both towards bases and acids. Thus, the product can be easily purified. Similar moieties that may be used in the described strategy include: substituted N-succinimido moieties, N-maleimido moiety, substituted N-maleimido moieties, and N-dithiasuccinimido moiety. The R groups each independently represent a sub- Amino group of 5'-methoxytrityl-2'-deoxy-2'-amino-nucleosides 1 can be selectively methoxyoxalylated with in situ prepared methyl oxalyl tetrazolide or, more preferably, with methyl oxalate, to form 2'-methoxyoxalamido precursor 2. Upon treatment with a proper nucleophile, such as an aliphatic primary or secondary amine (particularly an amino attached to an aliphatic carbon), ammonia or hydroxy anion, precursor 2 forms a corresponding 2'-modified nucleoside 3. Upon treatment with a mixture of different nucleophiles, the combinatorial library of 2'-modified nucleosides may be produced.

B. From N-succinimido precursor. A mechanism by which the present invention may be practiced is demonstrated below. Although specific groups are demonstrated in this mechanism, the invention is not limited thereto.

Amino group of 3',5'-TIPDS (1,1,3,3-tetraisopropyldisiloxane-1,3-yl) protected nucleosides 7 can be succinilated with in situ prepared succinyl tetrazolide to form 2'-N-succinimido precursor 8. Upon treatment with a proper nucleophile, such as a primary or secondary amine (particularly attached to an aliphatic carbon), ammonia or hydroxy anion, precursor 8 forms a corresponding 2'-modified nucleoside 9. Upon treatment with a mixture of different nucleophiles, the combinatorial library of 2'-modified nucleosides may be produced.

2. Functionally Modified Oligonucleotides

A. From methoxyoxalamido precursors. It has been previously demonstrated by Alul et al., "Oxalyl-CPG: a Labile Support for Synthesis of Sensitive Oligonucleotide derivatives," *Nucl. Acids Res.*, 19: 1527–1532 (1991), that an alkoxyoxalamidoalkyl moiety is stable towards the reagent used in solid-phase phosphoramidite synthesis. In particular, oxalyl group were used to anchor nucleosides to amino-derivatized CPG. Thus, phosphoramidite 4, which can be easily prepared from 2'-methoxyoxalamido nucleoside 2 by standard phosphitilation, can be incorporated into an oligonucleotide molecule during, for example, solid-phase synthesis. After the synthesis, functionally modified oligonucleotides can be prepared by treatment of the support-bound oligonucleotide precursor with a desirable modifier or linker. Backbone modified (phosphorothioates, methyl-phosphonates, etc.) FMOs can also be prepared by described strategy.

The methoxyoxalamido modification may also be introduced at positions other than the 2'-position. However, 2' modification may alter the hybridization properties of an oligonucleotide to a lesser extent than modification at a nucleobase or along the phosphate backbone.

B. From N-succinimido precursor. Phosphoramidite 12 can be prepared from nucleoside 8, for example, by a standard sequence of 3',5'-deprotection (compound 10), 5'-dimethoxytritylation (compound 11) and 3'-phosphitilation reactions, such as in the mechanism described below. The phosophoramidite 12 can then be incorporated into an oligonucleotide molecule during, for example, solid-phase synthesis. After the solid-phase synthesis, FMO can be prepared by treatment of the support-bound oligonucleotide precursor with a desirable modifier or linker.

3. 2'-Modified Oligonucleotides and Polynucleotides and Their Combinatorial Libraries 2'-Methoxyoxalamido and 2'-succinimido oligonucleotide precursors can be synthesized from monomers 4 and 12 by, for example, phophoramidite solid-phase synthesis. Being treated with a nucleophile, these precursors, as well as the other precursors taught herein, will produce corresponding 2'-modified oligonucleotides. A broad range of 2'-modified oligonucleotides can be prepared from a single 2'-methoxyoxalamido or 2'-succinimido oligonucleotide precursor.

If a precursor oligonucleotide is treated with mixtures of different nucleophiles, 2'-modified oligonucleotide combinatorial libraries can be created. These combinatorial libraries should be useful for many applications, for instance, for the search of powerful antisense/antigene drugs. This is particularly important because of the instability of natural oligonucleotides towards enzymes, such as nucleases. Backbone modified (phosphorothioates, methyl-phosphonates, etc.) 2'-modified oligonucleotides and their combinatorial libraries can also be prepared by the described strategy.

Further 2'-modified polynucleotides can be obtained using the 2'-methoxyoxalamido, 2'-succinimido and the other precursors taught herein.

4. Non-nucleoside Phosphodiester oligomers and Polymers and Their Combinatorial Libraries Methoxyoxalamido and N-succinimido moieties may also be part of different diol systems. Being DMT-protected at one hydroxy and phophitilated at another, such synthons can be used in, for example, phophoramidite solid-phase synthesis to produce non-nucleoside oligomer precursors. These precursors will produce, upon treatment with an appropriate nucleophile, non-nucleoside phosphodiester oligomers or polymers, or, upon treatment with mixtures of different nucleophiles, non-nucleoside phosphodiester oligomer or polymer combinatorial libraries. Backbone modified (phosphorothioates, methylphosphonates, etc.) non-nucleoside phosphodiester oligomers and their combinatorial libraries can also be prepared by the described strategy.

Any organic monomer unit can be used to form oligomer and polymers by the process taught herein as long as the monomer units are diols and contain or can be modified to contain a primary or secondary amine.

EXAMPLES

1. Synthesis of 5'-O-Dimethoxytrityl-2'-Methoxyoxalamido-2'-Deoxyuridine and its reaction with different nucleophiles 5'-O-Dimethoxytrityl-2'-amino-2'-deoxyuridine 1 is prepared as taught in Polushin, et al., "Synthesis of Oligonucleotides Containing 2'-Azido- and Amino-2'-Deoxyuridine Using Phosphotriester Chemistry," Tetrahedron Letters, 37: 3227–3230 (1996), incorporated herein by reference.

5'-O-Dimethoxytrityl-2'-methoxyoxalamido-2'-deoxyuridine may then be prepared in one of two ways proceeding from in situ prepared methyl oxalyl tetrazolide (A) or from commercially available methyl oxalate (B).

A. To 545 mg (1 mmol) of 5'-O-dimethoxytrityl-2'-amino-2'-deoxyuridine 1 in 10 ml of $CH_2Cl_2$, 2.7 ml of 0.45M methyl oxalyl tetrazolide solution in $CH_3CN$ is added. (The methyl oxaly tetrazolide solution is prepared in situ by mixing 0.45M tetrazole in $CH_3CN$ (1.2 eq) with methyl oxalyl chloride (1 eq) and 2,4,6-collidine (1 eq), and stirring at room temperature for 30 minutes.) 2.8 ml diisopropylethylamine (2 eq) is then added and the reaction mixture is left at room temperature for 15 minutes. 40 ml of $CH_2Cl_2$ is added and the reaction mixture is extracted with 50 ml of 1M TEAB. The organic phase is dried with $Na_2SO_4$, concentrated and chromatographed over silica gel to yield 410 mg (65% yield) of 5'-O-dimethoxytrityl-2'-methoxyoxalamido-2'-deoxyuridine 2.

B. Alternatively, 545 mg (1 mmol) of 5'-O-dimethoxytrityl-2'-amino-2'-deoxyuridine 1 is added to 590 mg (5 eq) of methyl oxalate in 10 ml of MeOH. The reaction mixture is stirred for 3 hours at room temperature. 50 ml of $CH_2Cl_2$ are added and the reaction mixture is extracted with 50 ml of 1M TEAB. The organic phase is dried with $Na_2SO_4$, concentrated and chromatographed over silica gel to yield 570 mg (90% yield) of 5'-O-dimethoxytrityl-2'-methoxyoxalamido-2'-deoxyuridine 2.

The spectral data for 2 is as follows: MS ESI (positive mode): 654.26 (M+Na$^+$), 1285.45 (2M+Na$^+$), calc. M=631.22; $^1$H-NMR (200 MHz, DMSO-d6): δ 11.32 (s, 1H, NH (U)), 8.54 (d, 1H, 2'-NH), 7.65 (d, 1H, H-6 (U)), 7.45–7.15 (m, 9H, H-Ar (DMT)), 6.87 (d, 4H, H-Ar (DMT)), 5.97 (d, 1H, H-1'), 5.86 (d, 1H, 3'-OH), 5.46 (d, 1H, H-5 (U)), 4.57 (dd, 1H, H-2'), 4.22 (dd, 1H, H-3'), 4.04 (dd, 1H, H-4'), 3.78 (s, 3H, COCOOCH$_3$), 3.71 (s, 6H, OCH$_3$ (DMT)), 3,36–3.12 (m, 2H, CH$_2$-5').

The 2'-methoxyoxalamido group in nucleoside 2 undergoes rapid transformation upon treatment with different nucleophiles. Compound 2 (0.1M CH$_2$Cl$_2$ solution) is treated with excess (50–100 eq) LiOH (1M aqueous-methanolic solution), methanolic ammonia (saturated at 0° C.), ethanolamine (EA), ethylenediamine (EDA), and 1,12-diaminododecane (DAD, 0.5M pyridine solution) to produce compounds within 3, as demonstrated in the mechanism below.

Imidazolyl-Linked Synthons and 3'-Conjugated Thymidine Derivatives," et al., *J. Org. Chem.*, 58: 4606–4613 (1993), incorporated herein by reference, except that the aqueous workup is omitted and the reaction mixture in CH$_2$Cl$_2$ is directly loaded onto a silica gel column. Elution with a pyridine/hexane/ethyl acetate mixture (0.5/10/89.5, v/v/v) afforded pure phosphoramidite 4 in 80% yield. MS ESI data for 4 (positive mode) is: 933.59 (M+Et$_3$NH$^+$), 832.48 (M+H$^+$), 854.42 (M+Na$^+$), calc. M=831.32.

Purified 4 (2 eq) is coupled with 5'-HO-T-3'-O-DMT (purchased from Glen Research) (1 eq) in CH$_3$CN (0.15–0.20M in 4) in the presence of tetrazole (5 eq) as a catalyst. Under these conditions the coupling reaction reaches completion in less than 5 minutes providing, after oxidation with iodine (Oxidizer Solution, DNA Synthesis Reagent, PerSeptive Biosystems), the desired diastereomeric phosphotriester dimer 5 in 80% isolated yield.

The diastereomers are further separated by preparative TLC and characterized. Selected spectral data for 5 include: MS ESI (positive mode): upper isomer: 1313.52 (M+Na$^+$), The products are purified by preparative TLC. As expected, efficient derivatization occurred with all nucleophiles. As indicated above, all but one of the modified nucleosides are formed nearly instantaneously, that is, in <1 minute, and quantitatively. In the case of the bulky DAD group, the reaction time is slightly longer, that is, ~3 min, and about 5% of a disubstituted product is formed in addition to the expected nucleoside. MS ESI data (positive mode) for 3 is: a: 662.19 (M+2Na$^+$), 719.35 (M+Et$_3$NH$^+$+H$^+$), 820.42 (M+2Et$_3$NH$^+$), calc. M=616.19; b: 639.21 (M+Na$^+$), 718.33 (M+Et$_3$NH$^+$), calc. M=616.22; c: 683.29 (M+Na$^+$), calc. M=660.24; f: 800.37 (M+H$^+$), calc. M=799.42.

2. Synthesis of 5'-DMT-2'-NHCOCOOCH$_3$-2'-dU-p (CE)-T-3'-DMT and its reaction with different nucleophiles Phosphitylation of 2 is accomplished conventionally, as taught in Polushin et al., "Synthesis and Characterization of lower isomer: 1313.51 (M+Na$^+$), calc. M=1290.42; $^1$H-NMR (200 MHz, DMSO-d6): upper isomer: δ 11.41 (s, 1H, NH (U)), 11.24 (s, 1H, NH (T)), 9.31 (d, 1H, 2'-NH (U)), 6.87 (t, 4H, H-Ar (DMT)), 5.37 (d, 1H, H-5 (U)), 3.71 (s, 12H, OCH$_3$ (DMT)), 3.68 (s, 3H, COCOOCH$_3$), lower isomer: δ 11.44 (s, 1H, NH (U)), 11.26 (s, 1H, NH (T)), 9.35 (d, 1H, 2'-NH (U)), 6.86 (d, 4H, H-Ar (DMT)), 5.43 (d, 1H, H-5 (U)), 3.75 (s, 3H, COCOOCH$_3$), 3.68 (m, 12H, OCH$_3$ (DMT)); $^{31}$P-NMR (200 MHz, DMSO-d6): upper isomer: δ-2.38, lower isomer: δ-1.58.

The phosphotriester dimer 5 is treated with excess (50–100 eq) of LiOH (1M aqueous-methanolic solution), methanolic ammonia (saturated at 0° C.), ethanolamine (EA), ethylenediamine (EDA), and 1,12-diaminododecane (DAD, 0.5M pyridine solution). In this case, however, the reaction time is increased to 30 minutes to ensure complete removal of β-cyanoethyl phosphate protecting group. Again, quantitative formation of phosphodiesters 6 is observed. Treatment with DAD resulted in a small amount, <5% by TLC, of disubstituted product along with the expected dimer. Selected spectral data for 6 include: MS ESI (positive mode) : 1428.68 (M+H+Na), 1406.63 (M+2H), calc M=1404.58; $^1$H-NMR (200 MHz, DMSO-d6): δ 7.67 (s, 1H, H-6 (T)), 7.60 (d, 1H, H-6 (U)), 7.45–7 11 (m, 18H, H—Ar (DMT)), 6.84 (t, 8H, H—Ar (DMT)), 6.24 (dd, 1H, H-1' (T)), 5.94 (d, 1H, H-1' (U)), 5.35 (d, 1H, H-5 (U)), 3.70 (d, >6H, OCH$_3$ (DMT)), 3.67 (s, >6H, OCH$_3$ (DMT)), 1.70 (s, >3H, CH$_3$ (T)), 1.20 (br. s, 20H, (CH$_2$)$_{10}$ (DAD)).

3. Synthesis of 5'-OH-U[2'-NHCOCOHN(CH$_2$)$_{12}$NH$_2$]p (Tp)$_8$T-OH-3'.

The novel convergent strategy is next established at the oligonucleotide level. A 10-mer consisting of nine thymidines and one 2'-methoxyoxalamido-2'-deoxyuridine at the 5'-end is synthesized by automated solid-phase β-cyanoethyl phosphoramidite chemistry (3×1 μmol scale) on an Expedite DNA Synthesizer. Coupling time for phosphoramidite 4 (0.1M CH$_3$CN solution) is 33 minutes, which provided a coupling yield of 75–80% based on dimethoxytrityl cation release. The reason for the rather poor yield is most likely attributable to stearic hindrance by the rigid 2'-methoxyoxalylamido residue.

Detritylated support-bound decamer is treated with DAD (0.5M pyridine solution, 500 μl) for 3 hrs at room temperature. Aqueous ammonia (500 μl) is subsequently added and the reaction mixture is kept for another hour to ensure complete cleavage of the succinate linkage and removal of β-cyanoethyl phosphate protecting groups. Finally, the reaction mixture is desalted over Sephadex G25 to give 198 A260 units of crude material consisting primarily of the desired derivatized 10-mer, 5'-HO-U[2'-NHCOCONH(CH$_2$)$_{12}$NH$_2$](Tp)$_8$T-OH-3', and the unreacted 9-mer 5'-HO-(Tp)$_8$T-OH-3'. A total of 60 ODUs (30%) of the DAD-oligonucleotide conjugate is isolated by denaturating 20% PAAG electrophoresis and the structure of the conjugate is confirmed by a variety of analytical methods.

Figure 1:
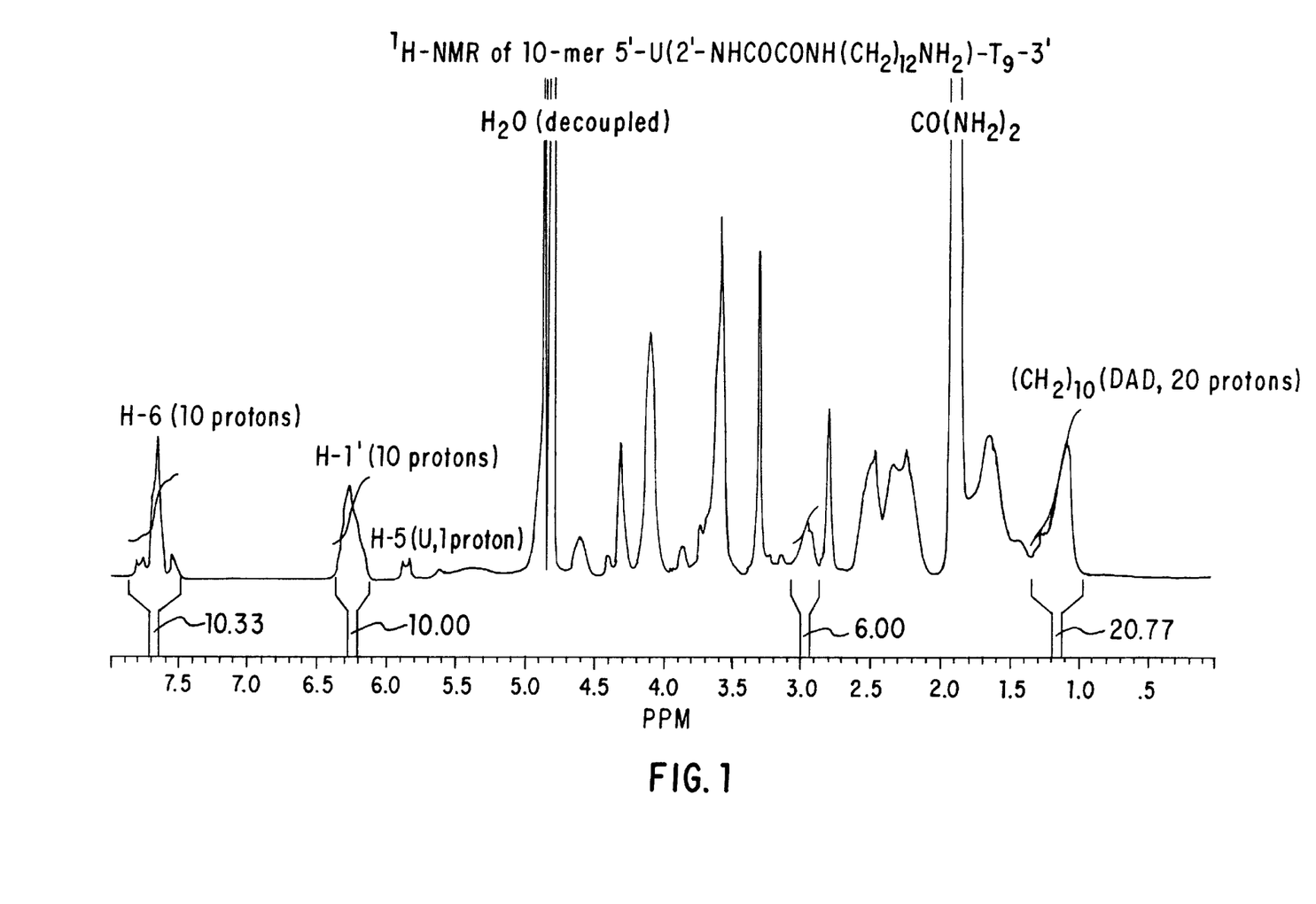
FIG. 1 demonstrates the 200 mHz $^1$H-NMR spectrum of the 10-mer 5'-HO-U[2'-NHCOCONH(CH$_2$)$_{12}$NH$_2$](Tp)$_8$T-OH-3', conforming the incorporation of the DAD residue.

Enzymatic digestion and base composition analysis revealed two nucleoside components in approximately 9:1 ratio having HPLC retention times identical to authentic thymidine and 2'-NHCOCONH(CH$_2$)$_{12}$NH-$_2$-2'-dU. Delayed extraction MALDI-TOF MS analysis, as taught in Smirnov, I.P. et al., Anal. Biochem. (1996), incorporated herein by reference, yielded a 255.5 mass difference between the DAD-modified 10-mer and a standard 5'-HO-(Tp)$_9$T-OH-3', in agreement with the calculated mass difference of 255.2 Da. Finally, the structure is confirmed by $^1$H-NMR analysis, as demonstrated in FIG. 1.

4. Synthesis of 5'-OH-(Tp)$_5$(U[2'-NHCOCOOCH$_3$]p)$_5$(Tp)$_4$T-3'-CPG and its derivatization with LiOH, methylamine, ethanolamine and ethylenediamine Coupling of phosphoramidite 4 during solid-phase synthesis is rather poor if standard tetrazole is used as a catalyst: only 75–80% coupling yield at 33 minutes coupling time. Such low yield does not allow incorporation of several (practically more than 3) modified nucleosides. Coupling yield, however, is considerably improved if 1-phenyl-1H-tetrazole-5-thiol (PTT) is used as a catalyst. It is further improved by using a double mode coupling protocol.

By this protocol, CPG-immobilized 15-mer, 5'-OH-(Tp)$_5$(U[2'-NHCOCOOCH$_3$]p)$_5$(Tp)$_4$T-3'-CPG, is synthesized using automated solid-phase cyanoethyl phosphoramidite chemistry on 1 μmole scale on an Expedite DNA Synthesizer. 0.1M PTT in CH$_3$CN is used as an activator solution. 0.1M solutions of phosphoramidites (T and 2'-NHCOCOOCH$_3$-2'-U) in CH$_3$CN are used. Synthesis was performed using the 1 μmole protocol provided by the DNA synthesizer's sapplier (PerSeptive Biosystems), except during incorporation of 2'-methoxyoxalamido-2'-deoxyuridine phosphoramidite 4, two consecutive couplings, 2.5 minutes each, divided only by 40 seconds of washing with CH$_3$CN, are used.

Figure 2:
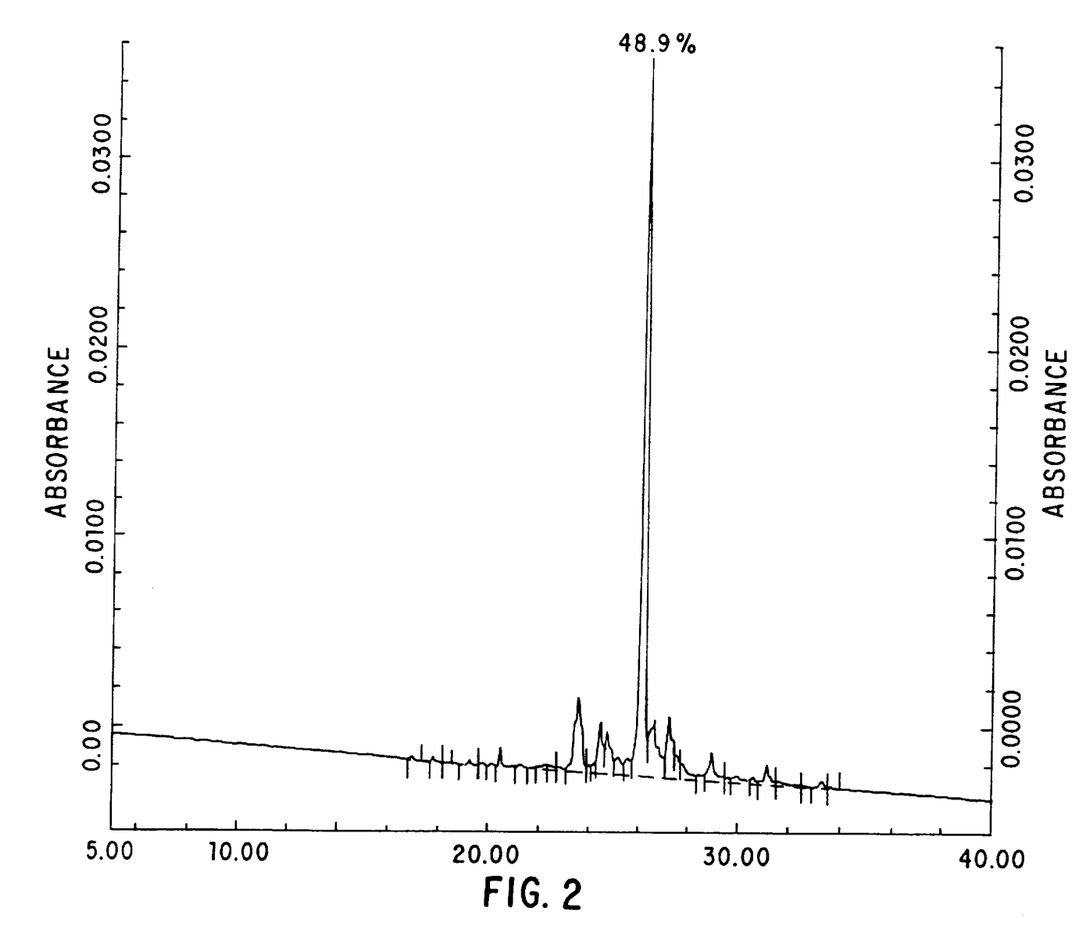
FIG. 2 demonstrates capillary electrophoresis of ethylenediamine modified 15-mer, 5'-OH-(Tp)$_5$(U[2'-NHCOCONH(CH$_2$)$_2$NH$_2$]p)$_5$(Tp)$_4$T-3'-CPG.

After solid-phase synthesis the derivatized CPG-support is divided into four portions (5–10 mg each) and each portion is treated with one of LiOH (1M aqueous solution, 200 μl), methylamine (2M methanolic solution, 200 ul), ethanolamine (200 μl) and ethylenediamine (200 μl) for 1 hour at room temperature. Water (800 μl) is added and the reaction mixtures are left for 30 minutes and then desalted over Sephadex G-25. In the case of LiOH, the reaction mixture is desalted right after water addition. Crude ethylenediamine modified 15-mers are purified by polyacrylamide gel electrophoresis, as demonstrated in FIG. 2.

5. Synthesis of 5'-O-dimethoxytrityl-2'-N-succinimido-2'-deoxyuridine and its reaction with different nucleophiles To 545 mg (1 mmol) of 5'-O-dimethoxytrityl-2'-amino-2'-deoxyuridine 1 in 10 ml of CH$_2$Cl$_2$, 4.2 ml of 0.36M succinyl tetrazolide solution in CH$_3$CN is added. (The succinyl tetrazolide solution is prepared in situ by mixing of 3.51 g (50 mmol) of tetrazole in 50 ml of CH$_3$CN with 2.2 ml of succinyl chloride (20 mmol) and 5.28 mol of 2,4,6-collidine (40 mmol), and stirring at room temperature for 30 minutes.) After 15 minutes, 40 ml of CH$_2$Cl$_2$ is added and the reaction mixture was extracted with 50 ml of 1M TEAB. The organic phase is dried with Na$_2$SO$_4$, concentrated and separated by preparative TLC on silica gel to yield 94 mg (15%) of 5'-O-dimethoxytrityl-2'-N-succinimido-2'-deoxyuridine. The yield is improved by the use of 3',5'-TIPDS as described above.

Reaction of 5'-O-dimethoxytrityl-2'-N-succinimido-2'-deoxyuridine with nucleophiles (cycle opening) proceeds nearly instantaneously and quantitatively.

6. Synthesis of 2'-methoxyoxalamido-2'-deoxyguanosine and its reaction with different nucleophiles 2'-Amino-2'-deoxyguanosine is prepared as taught in Benseler et al., "Synthesis of Suitably-Protected Phosphoramidites of 2'-Fluoro-2'-Deoxyguanosine and 2'-Amino-2'-Deoxyguanosine for Incorporation into Oligonucleotides," Nucleosides & Nucleotides, 11:1333–1351 (1992), which is incorporated herein by reference.

283 mg (1 mmol) of 2'-amino-2'-deoxyguanosine is added to 590 mg (5 mmol) of methyloxalate in 10 ml of MeOH. 50 ml of $CH_2Cl_2$ are added and the reaction mixture is extracted with 50 ml of 1M TEAB. The organic phase is dried with $NA_2SO_4$, concentrated and chromatographed over silica gel to yield 250 mg (90% yield) of a white solid, which is 2'-methoxyoxalamido-2'-deoxyguanosine.

2'-methoxyoxalamido-2'-deoxyguanosine (0.1M $CH_2Cl_2$ solution) is treated with excess LiOH, methanolic ammonia, ethanolamine, ethylenediamine, and 1,12-diaminododecane. The 2'-methoxyoxlamido group in the compound undergoes rapid transformation upon treatment with the different nucleophiles.

In conclusion, the utility of 2'-methoxyoxalamido or 2'-succinimido modification for the post synthetic introduction of various functional additives into an oligonucleotide molecule has been demonstrated. Alternative precursor compounds and routes to the synthesis of FMOs through 2'-methoxyoxalamido oligonucleotides generated in situ from 2'-amino precursors are also possible.

What is claimed is:

1. A compound having the formula (III):

A—R'  (III)

where A represents a nucleoside or nucleotide, R' is selected from the group consisting of: —NRCOCONu, —NHCOCR₂CR₂CONu, —NHCOCR═CRCONu, —NHCOSSCONu, —NRCOCOOCR₃, each R independently represents H or a substituted or unsubstituted alkyl group, and Nu represents a nucleophile, or a salt of said compound.

2. The compound or salt thereof according to claim 1, wherein the nucleophile is selected from the group consisting of —O⁻, an amino group, a primary amino group and a secondary amino group.

3. The compound or salt thereof according to claim 1, wherein said nucleoside or nucleotide is part of an oligomer or polymer.

4. The compound or salt thereof according to claim 1, wherein said nucleoside or nucleotide is a modified nucleoside or nucleotide.

5. The compound or salt thereof according to claim 1, wherein R' is selected from the group consisting of: —NRCOCONu, —NHCOCR₂CR₂CONu, —NHCOCR═CRCONu and —NHCOSSCONu.

6. The compound or salt thereof according to claim 1, wherein R' is selected from the group consisting of: —NRCOCOOCR₃, 7. The compound or salt thereof according to claim 1, said compound having the formula (II):

(II)

wherein B is a purine or pyrimidine moiety and each X independently represents H, a group that protects a hydroxy group, a $(PO_3)_m^{-2}$ group wherein m is an integer of 1–3, a group reactive to link hydroxy groups, or a phosphodiester linkage to another compound.

8. The compound or salt thereof according to claim 7, wherein at least one X represents a dimethoxytrityl group.

9. The compound or salt thereof according to claim 1, wherein said compound is a nucleoside joined through a phosphodiester linkage to at least one other nucleoside to form a oligonucleotide or a polynucleotide.

10. A method for attaching a nucleophile to a nucleoside or nucleotide, comprising:

reacting a first compound containing a first moiety selected from the group consisting of —COCOOCR₃, —COCR₂CR₂CO—, —COCR═CRCO— and —COSSCO— with a nucleoside or nucleotide containing a primary or secondary amine to form a second compound containing a second moiety selected from the group consisting of —NRCOCOOCR₃, said first moiety attaching to a nitrogen of the amine to form said second moiety, wherein each R independently represents H or a substituted or unsubstituted alkyl group;

reacting a protonated nucleophile (HNu) with the second moiety of said second compound to form a third compound containing a third moiety selected from the group consisting of: —NRCOCONu, —NHCOCR$_2$CR$_2$CONu, —NHCOCR=CRCONu and —NHCOSSCONu.

11. The method according to claim 1, wherein the amine is a primary amine where the first moiety is —COCR$_2$CR$_2$CO—, —COCR=CRCO— or —COSSCO—.

12. The method according to claim 1, wherein the protonated nucleophile is selected from the group consisting of ammonia, primary amines, secondary amines and a hydroxy group.

13. The method according to claim 10, wherein said primary or secondary amine is attached to said nucleoside or nucleotide at a position on the sugar.

14. A method for forming an oligonucleotide or polynucleotide, comprising:

reacting a compound containing a first moiety selected from the group consisting of —COCOOCR$_3$, —COCR$_2$CR$_2$CO—, —COCR=CRCO— and —COSSCO— with a nucleoside or nucleotide containing a primary or secondary amine to form a nucleoside or nucleotide containing a second moiety selected from the group consisting of —NRCOCOOCR$_3$, said first moiety attaching to a nitrogen of the amine to form said second moiety, wherein each R independently represents H or a substituted or unsubstituted alkyl group;

reacting said nucleoside or nucleotide containing a second moiety with at least one other nucleoside or nucleotide to form an oligonucleotide or polynucleotide;

reacting a protonated nucleophile (HNu) with the second moiety to form a third moiety in said oligonucleotide or polynucleotide, said third moiety being selected from the group consisting of: —NRCOCONu, —NHCOCR$_2$CR$_2$CONu, —NHCOCR=CRCONu and —NHCOSSCONu.

15. The method according to claim 14, wherein the amine is a primary amine where the first moiety is —COCR$_2$CR$_2$CO—, —COCR=CRCO— or —COSSCO—.

16. The method according to claim 14, wherein the protonated nucleophile is selected from the group consisting of ammonia, primary amines, secondary amines and a hydroxy group.

17. The method according to claim 14, wherein said primary or secondary amine is attached to said nucleoside or nucleotide at a position on the sugar.

18. The method according to claim 14, wherein 1-phenyl-1H-tetrazole-5-thiol is used as a catalyst during said step in which the nucleoside or nucleotide containing a second moiety reacts with at least one other nucleoside or nucleotide to form an oligonucleotide or polynucleotide.

19. The method according to claim 14, wherein said nucleoside or nucleotide containing a second moiety reacts with at least one other nucleoside or nucleotide to form an oligonuleotide or polynucleotide using double mode phosphitilation.

* * * * *

UNITED STATES PATENT AND TRADEMARK OFFICE
CERTIFICATE OF CORRECTION

PATENT NO. : 5,902,879
DATED : May 11, 1999
INVENTOR(S) : Nikolai N. Polouchine

It is certified that error appears in the above-identified patent and that said Letters Patent is hereby corrected as shown below:

Column 21,
Line 4, change "1" to -- 10 --.
Line 8, change "1" to -- 10 --.

Signed and Sealed this

First Day of January, 2002

Attest:

JAMES E. ROGAN
*Attesting Officer*    *Director of the United States Patent and Trademark Office*